United States Patent [19]

Pinto

[11] 4,309,359
[45] Jan. 5, 1982

[54] ENERGY PROCESS IN METHANOL SYNTHESIS

[75] Inventor: Alwyn Pinto, Stockton-on-Tees, England

[73] Assignee: Imperial Chemical Industries Limited, London, England

[21] Appl. No.: 860,311

[22] Filed: Dec. 12, 1977

[30] Foreign Application Priority Data

Dec. 15, 1976 [GB] United Kingdom ............... 52304/76

[51] Int. Cl.³ ............................................. C07C 29/15
[52] U.S. Cl. .................................. 518/705; 48/197 R;
48/214 R; 48/214 A; 252/373; 429/16; 429/17;
60/205; 518/715; 518/728
[58] Field of Search ........ 260/449.5, 449 M, 449.6 M;
252/373; 48/197 R, 214 R, 214 A; 429/16, 17

[56] References Cited

U.S. PATENT DOCUMENTS

| | | | |
|---|---|---|---|
| 3,469,944 | 9/1969 | Bocard et al. | 48/214 A |
| 3,480,417 | 11/1969 | Setzer | 48/214 R |
| 3,501,516 | 3/1970 | Parrish | 252/373 |
| 3,598,527 | 8/1971 | Quartulli et al. | 260/449.5 |
| 3,993,457 | 11/1976 | Cahn et al. | 48/197 R |

FOREIGN PATENT DOCUMENTS

| | | | |
|---|---|---|---|
| 1039382 | 8/1966 | United Kingdom | 252/373 |
| 1484366 | 9/1977 | United Kingdom | 260/449.5 |

*Primary Examiner*—Howard T. Mars
*Attorney, Agent, or Firm*—Cushman, Darby & Cushman

[57] ABSTRACT

In a process in which, after product recovery, an off-gas containing hydrogen and/or carbon monoxide is produced, energy economy is improved by reacting the off-gas in a fuel cell. The resulting electricity is preferably used for driving small machines in the process. The process is especially useful for producing methanol from natural gas feedstock and then includes the steps of methanating the off-gas and letting it down in an engine before passing it to a fuel cell.

9 Claims, 1 Drawing Figure

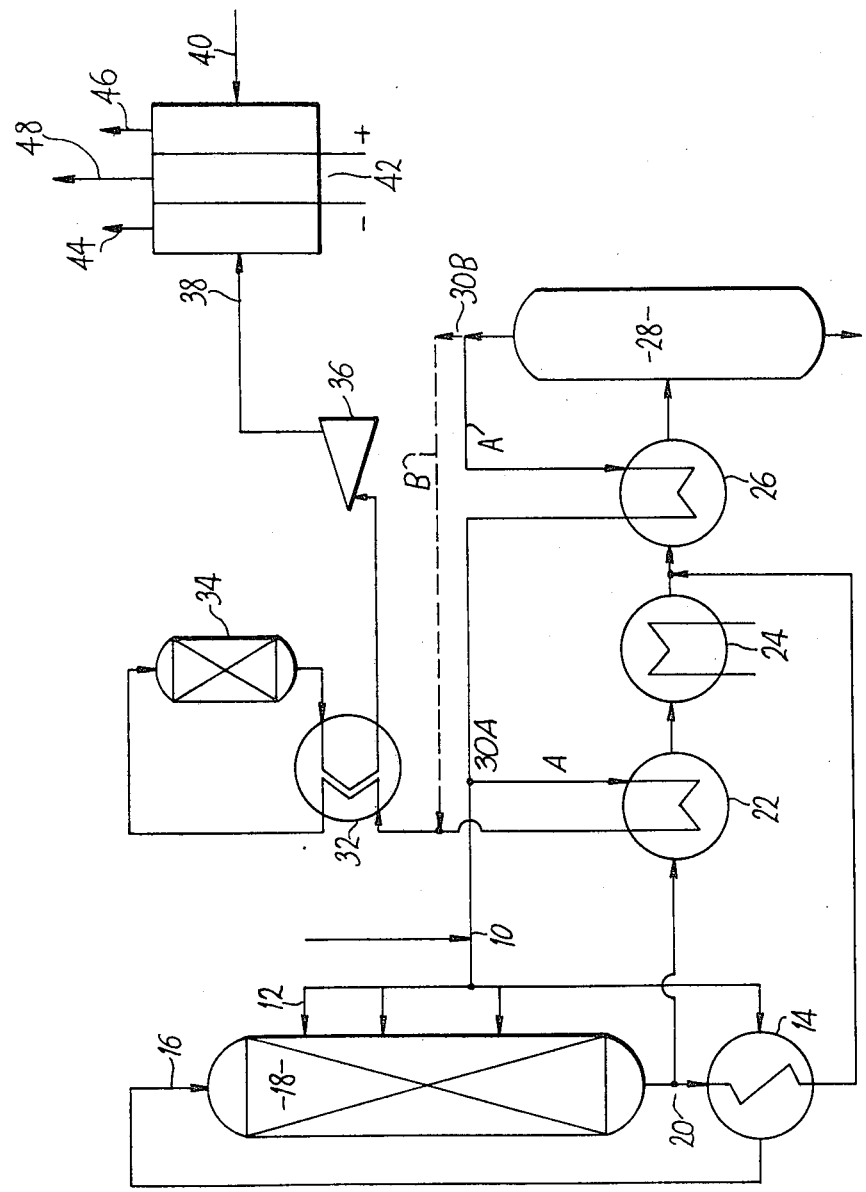

ENERGY PROCESS IN METHANOL SYNTHESIS

This invention relates to energy recovery and in particular to a chemical process in which an off-gas having fuel value is treated to produce useful energy.

According to the invention a catalytic process which is dehydrogenation of an alcohol or hydrocarbon or is hydrogenation comprises the stages of
  (a) passing the reactants over a catalyst for the process;
  (b) condensing and separating a liquid product; and
  (c) passing out an off-gas comprising carbon monoxide and/or hydrogen; and is characterized by generating electricity by oxidising the off-gas in a fuel cell.

Among the processes operable according to the invention are ammonia synthesis, carbon oxide hydrogenations to normally liquid products, ketone manufacture by alcohol dehydeogenation and hydrocarbon transformations such as cracking, aromatisation and olefin manufacture, which involve dehydrogenation. Ammonia synthesis is especially suitable because its off-gas ("purge gas") contains only hydrogen, nitrogen, noble gases and (usually) methane, and can thus be reacted in any type of fuel cell. Off-gas from the alcohol dehydrogenation processes and hydrocarbon transformation processes may, however, contain carbon oxides and/or highly unsaturated hydrocarbons, depending on the extent of side-reactions and on whether the gas has been fractionated; consequently a cell should then be used that tolerates such constituents or steps should be taken (such as fractionation or, if their content is low, such as methanation) to remove them. Off-gases from carbon oxide hydrogenations, such as methanol synthesis or synthesis of liquid hydrocarbons or oxygenated hydrocarbons, contain substantial quantities of carbon oxides, but are or can readily be made suitable for reaction in some types of fuel cell, as will be described below.

In an ammonia synthesis process according to the invention the following stages are typically present:
  (a) generating a fresh synthesis gas containing nitrogen and hydrogen;
  (b) reacting the fresh synthesis gas, mixed with a recycle gas to be described, over an ammonia synthesis catalyst to effect partial conversion to ammonia;
  (c) cooling the catalyst effluent gas, and condensing ammonia from it;
  (d) recycling the gas after separating the ammonia and uniting it with fresh synthesis gas;
  (e) purging, usually between stages (b) and (c) or between stages (c) and (d), a minor proportion of the gas in order to prevent excessive build-up of the proportion of unreactive gases therein;
  (f) generating electricity by reacting the purge gas in one or more fuel cells.

The pressure for such a synthesis is typically in the range 100–500 atm. abs. and the temperature is typically 350°–430° C. at the catalyst inlet, 400°–500° C. at the catalyst outlet and in the range —30 to +40° C. (depending on the pressure) in the ammonia condensation stage. The synthesis gas generation usually involves a high temperature reaction (in the range 700°–1200° C.) of a carbonaceous fuel with steam and/or oxygen, followed by stages of carbon monoxide shift, carbon dioxide removal and final purification by methanation or cryogenic treatment. Procedures have been developed for recovering heat, preferably in the form of steam at 40–120 atm. abs. pressure, from the hot gases formed in the high temperature reaction and/or shift reaction and/or synthesis reaction. Such high pressure steam is advantageously let down in expansion engines driving the synthesis gas compressor and circulator in the process. If such steam engines are pass-out turbines their exhaust is used as process steam for synthesis gas generation.

In a carbon oxide hydrogenation process according to the invention the following stages are typically present:
  (a) generating a fresh synthesis gas containing hydrogen and either or both of carbon monoxide and carbon dioxide;
  (b) reacting the fresh synthesis gas, usually mixed with a recycle gas to be described, over a catalyst to effect partial conversion to synthetic hydrogenation products;
  (c) cooling the catalyst effluent gas and condensing products from it;
  (d) passing the gas left over after separating the products to further catalytic conversion, usually by recycling it and uniting it with fresh synthesis gas;
  (e) at a suitable point, for example between stages (b) and (c) or, more usually between (c) and (d), or after one or more further stages of synthesis and separation separate from stage (b), passing gas out of the synthesis system; and
  (f) generating electricity by reacting the passed-out gas in one or more fuel cells.

The pressure for such a process of methanol synthesis is typically in the range 10–400 atm. abs. and in particular in the range 10–150 atm. abs. if it is one of the recently developed syntheses over a copper-containing catalyst or 150–400 atm. abs. if it is one of the older processes over a zinc-chromite catalyst. The catalyst outlet temperatures for such processes are respectively 160°–300° C. (especially 190°–270° C.) and 300°–450° C. and typically in the range 0°–60° C. in the methanol condensation stage. The synthesis gas generation usually involves a high temperature reaction (in the range 700°–1200° C.) of a carbonaceous fuel with steam and/or oxygen, followed when necessary by stages in which the hydrogen to carbon oxides ratio is adjusted. The hydrogen to carbon oxides ratio is usually greater than stoichiometric because this enables the rate of the synthesis reaction to be greater and, when the fuel contains more than 2 hydrogen atoms per carbon atom and is reacted without oxygen, enables the cost of carbon oxides addition to be avoided. Heat recovery is similar to that used in ammonia synthesis, except that in copper-catalysed methanol synthesis it is impracticable to generate high pressure steam by cooling the gas in or leaving the synthesis catalyst; instead, medium pressure steam or boiler feed water is produced if heat is to be recovered from such a gas.

When the off-gas is at superatmospheric pressure, it is preferably treated to effect further energy recoveries by heating it by heat exchange with a hot stream in the catalytic process or synthesis gas generation process and/or by letting it down in an expansion engine, especially after such heating.

When the off-gas contains carbon monoxide, as in a carbon oxide hydrogenation such as methanol synthesis, it is preferably reacted with steam over a shift catalyst such as iron-chrome or copper/zinc oxide to convert carbon monoxide to hydrogen, before passing it to the fuel cell. The shift catalyst may be followed by steps of carbon dioxide removal and carbon oxides clean-up (by e.g. methanation) if the fuel cell used is one in which carbon oxides are objectionable. If desired, carbon monoxide can be removed by selective catalytic oxidation with oxygen, suitably added as air. Carbon oxide removal, if required, can be effected by the usual liquid absorbents such as amines, alkali carbonates, copper liquor or cuprous aluminum chloride, depending on whether CO or $CO_2$ or both should be removed.

As an alternative to such steps involving shift conversion or as additional purification, hydrogen can be separated using for example a palladium membrane or molecular sieve adsorption or cryogenic fractionation and fed to the fuel cell. When such a separation process is used, the carbon oxide or oxides can be recycled to the methanol synthesis stage.

When the process produces an off-gas containing hydrogen in excess of the quantity that can be methanated by the carbon oxides present or can saturate unsaturated hydrocarbons present, it is prepared for reaction in the fuel cell preferably by reacting it over a hydrogenation catalyst. This procedure is especially suitable for the purge gas from a methanol synthesis process operated with excess hydrogen, for example using a synthesis gas made by catalytic reaction of steam with a normally gaseous hydrocarbon, especially natural gas. In such a process the whole purge gas is methanated. This can be effected over a general methanation catalyst such as supported nickel or cobalt, in which event both CO and $CO_2$ are reacted, or over a selective catalyst such as supported ruthenium, in which event CO is reacted but not $CO_2$. Methanation raises the gas temperature and is thus valuable if the fuel cell is of the type operating at high temperature or if the gas is to be let down in an expansion engine. It is also a convenient way of removing carbon oxides.

The invention is especially valuable in a process in which major mechanical power requirements, such as in compression and/or circulation of synthesis gas for a hydrogenation process, are provided by pass-out steam turbines. In such processes the steam for such turbines is usually the product of a waste heat boiler in the synthesis gas generation section. Part of the major requirement and also of the minor power requirement, such as in pumps for air, hydrocarbon feed, boiler feed water and $CO_2$ removal solutions and fans for cooling air and combustion gases, have been previously provided by small or condensing turbines, which are less thermally efficient (about 30%) than pass-out turbines (75-80%); "small" means 1 megawatt or less. By the use of the invention minor requirements are provided from the electricity generated by the fuel cell and also, if desired, by an engine in which passed-out gas is let down from synthesis pressure, and consequently the relatively inefficient small turbines are not used.

Many types of fuel cell can be used in the process of the invention. Cells using a liquid acid electrolyte and electrodes not poisoned by carbon oxides are applicable to all embodiments of the process. If electrodes poisoned by carbon monoxide such as platinum are used it can be removed as described above. Cells employing molten alkali metal carbonates as electrolyte are more suitable, because then operate at relatively high temperatures (e.g. 400°-700° C.) at which hydrogen-containing gas can be economically provided from a catalytic process of the types included in the invention: for such a cell the gas leaving an ammonia synthesis catalyst or methanated methanol synthesis pass-out gas can be used. For hot gases there can be used cells having solid electrolytes, for example zirconia/calcia or zirconia/yttria. The high temperature cells have the further advantage of producing steam as a by-product, which can be used in the process for e.g. heating a methanol distilation column or for the shift reaction.

Cells of the type being developed for public utility operation by for example, Pratt and Whitney Inc. are especially useful for the process of the invention, being designed for large output. The cell output may be used directly or via a pulsing system to give an alternating current output. A suitable cell system is described by Farris, Energy Dev. IEEE Power Engineering Society Papers, 1974, 42-46.

In a useful form of the invention, the gas fed to the fuel cell from a carbon oxide hydrogenation process such as methanol synthesis reacts in the cell to give a residual gas enriched in carbon oxides, and the residual gas is recycled to the hydrogenation process.

Since the predominant reaction in the fuel cell is oxidation of hydrogen, a residual gas enriched in other components, usually methane, with nitrogen and noble gases in ammonia synthesis or carbon oxides in carbon oxide hydrogenations, is produced by the cell. It can be used as a fuel, suitable for heating a primary reformer in synthesis gas generation or, if its inerts content is not too high, recycled to synthesis gas generation.

The oxidising component of the fuel cell is most conveniently air, and can be taken from the compressed air supply already present in the process if it includes a secondary reformer or an air-separation plant in its synthesis gas generation section.

A flowsheet of one preferred form of methanol synthesis process according to the invention is shown in the accompanying drawing.

Fresh synthesis gas is fed at point 10 where it mixes with a recycle gas stream from methanol separator 28. The mixed gas is fed to the synthesis reactor partly cold at quench inlets 12 and for the remainder via heat exchanger 14 to the reactor at inlet 16. Reaction takes place in catalyst bed 18, the temperature being controlled by cold gas injected at quench inlets 12. Hot reacted gas leaving the reactor is divided at 20 into two streams. One stream passes through purge gas heater 22 and then through exchanger 24, which is a water heater providing pressurised hot water feed to be used in boilers in synthesis gas generation (not shown). The other stream passes through feed gas preheater 14 in which it heats synthesis gas to catalyst inlet temperature and is then reunited with the first stream leaving water heater 24. The combined reacted gas stream is further cooled in recycle gas heater 26 possibly also in additional coolers not shown, until it reaches the dew point of methanol, and is passed into product separator 28. Aqueous methanol is taken off at the bottom of separator 28 and unreacted gas at the top, whence it passes by either of two paths to recycle and methanation. On path A, shown by the full line, it is heated in exchanger 26 and divided at point 30A into a recycle stream to point 10 and a purge stream via heater 22 to the inlet of exchanger 32. On path B, shown by the pecked line, the purge stream is taken at 30B instead of 30A and passed cold to the inlet of exchanger 32. In exchanger 32 the purge gas is heated by hot effluent from catalytic methanator 34. The methanated gas leaving exchanger 32 is still hot and is passed through turbine 36 in which it is expanded with cooling. The turbine effluent is fed to the anode of the fuel cell 38 (which represents a battery of fuel cells electrically connected in series), in which its hydrogen reacts with oxygen fed to the cathode at 40. Reaction of the purge gas produces a residual gas depleted in hydrogen and enriched in methane, which is withdrawn at 44 and passed to synthesis gas generation. If air is the source of oxygen, a gas depleted in oxygen is withdrawn at 46. If the fuel cell is of the high temperature type, steam is produced at 48 and passed to the re-boilers of the methanol distillation section or to boiler feed water heaters.

Although the flowsheet shows a quench-type reactor, it will be appreciated that it can be readily adapted to employ other types of reactor or succession of reactors in a once-through system. Furthermore it will be appreciated that variations are possible in the extent of heating the purge gas. The use of methanator 34 is preferred because it effects substantial removal of carbon oxides from the gas as well as increasing its temperature.

Turbine 36 can drive a compressor or pump in the plant directly, but preferably drives an electrical generator, thus providing, with fuel cell output 42, part of the power-supply for the electrically driven machines of the plant.

In a plant producing 1000 metric tons per day of methanol by steam reforming natural gas, removing excess steam by condensation, compressing the dry gas to 90 atm. abs. pressure and reacting it over a copper-containing catalyst, a purge gas at 35° with the following composition % v/v is taken at the rate of 1997.3 kg mol/hour:

$CO$: 2.05
$CO_2$: 2.5
$H_2$: 78.1
$CH_4$: 15.1
$N_2$ + inset gases: 1.98
$H_2O$: 0.03
methanol: 0.25
dimethyl ether: 0.017

It is passed through a supported nickel catalyst in a methanator to produce, at an outlet temperature of 326° C., 1814.2 kg mol/hour of a gas having the composition $H_2O$: 8.1
$CH_4$: 21.9
$H_2$: 67.8
$N_2$ + inert gases: 2.2

(The temperature 326° C. is measured at the exit of heater 32). This gas is let down through turbine 36 to 4 atm abs. pressure, temperature 126° C. and fed to fuel cell 38. The turbine drives a generator producing 3.3 megawatts of electricity. The fuel cell produces 30 megawatts and also 50 metric tons per hour of low pressure steam.

NOTE: This power output is that of the process following path B on the flowsheet. Following path A the temperature of the feed gas entering exchanger 32 would be conveniently 235° C. and that of the reacted gas entering turbine 36 thus about 526° C., so that a proportionately higher power output from turbine 36 would be obtained.

I claim:

1. In a process for producing methanol by the steps of:
    (a) reacting a methanol synthesis gas containing hydrogen and at least one of carbon monoxide and carbon dioxide over a methanol synthesis catalyst to effect partial conversion to methanol;
    (b) cooling the resulting partly reacted gas and separating methanol from it;
    (c) recycling unreacted gas from separation Step (b) to synthesis Step (a); and
    (d) purging a portion of unreacted gas whereby to prevent excessive build-up of the proportion of non-reacting gases in the synthesis gas,
  the improvement resulting in decreased energy consumption per unit of methanol output which comprises passing said purged gas to one or more fuel cells whereby to generate electricity by oxidation of hydrogen contained therein.

2. A process according to claim 1 in which the purge gas contains carbon monoxide and which includes a stage of reacting it with steam over a shift catalyst selected from the group consisting of iron-chrome and copper/zinc oxide to convert carbon monoxide to hydrogen, before passing said gas to the fuel cell.

3. A process according to claim 1 in which the methanol synthesis step is operated using excess hydrogen and the purge gas contains hydrogen in excess of the quantity that can be methanated by the carbon oxides contained in it, wherein said whole purge gas is methanated over a catalyst selected from the group consisting of supported nickel, supported cobalt and supported ruthenium and then passed to the said one or more fuel cells whereby to generate electricity by oxidation of the hydrogen still present after methanation.

4. A process according to claim 1 which comprises also recovering energy by letting-down said purge gas in an expansion engine before passing it to said one or more fuel cells.

5. A process according to claim 1 in which the fuel cell uses a liquid acid electrolyte and electrodes not poisoned by carbon oxides.

6. A process according to claim 1 in which the fuel cell employs molten alkali metal carbonates as electrolyte.

7. A methanol synthesis process according to claim 1 in which a gas enriched in carbon oxides is recovered from the fuel cell and recycled to the synthesis catalyst.

8. A process for producing methanol in a plant by the steps of:
    (a) generating methanol synthesis gas;
    (b) passing hot gases produced in synthesis gas generation through a waste heat boiler whereby to generate steam;
    (c) expanding such steam in one or more pass-out turbines;
    (d) compressing synthesis gas to synthesis pressure and circulating said gas through methanol synthesis, methanol separation and unreacted gas recycle, by means of one or more machines driven by said pass-out turbines;
    (e) purging a minor portion of said unreacted gas, whereby to prevent the build-up of an excessive concentration of non-reacting gases in said synthesis gas;
    (f) passing said purge gas to one or more fuel cells whereby to generate electricity by oxidation of hydrogen contained therein;
    (g) using such electricity to power one or more machines of the plant.

9. A process according to claim 8 wherein said methanol synthesis gas is generated by reacting a carbonaceous fuel with steam and/or oxygen at a temperature in the range 700°–1200° C.

* * * * *